United States Patent [19]

King

[11] 4,148,154
[45] Apr. 10, 1979

[54] COMPOSITE HORTICULTURAL SYSTEM

[75] Inventor: James H. King, Los Altos Hills, Calif.

[73] Assignee: Harry E. Aine, Palo Alto, Calif. ; a part interest

[21] Appl. No.: 830,436

[22] Filed: Sep. 6, 1977

[51] Int. Cl.² .......................... A01K 1/00; A01G 9/02
[52] U.S. Cl. ......................................... 47/58; 119/15; 47/66; 47/17; 47/14
[58] Field of Search .................... 119/1, 15; 47/66, 19, 47/17, 14

[56] References Cited

U.S. PATENT DOCUMENTS

| 419,370 | 1/1890 | Smart | 47/19 |
|---|---|---|---|
| 2,527,214 | 10/1950 | Graves | 119/15 X |
| 3,129,692 | 4/1964 | Sanderson | 119/15 |
| 3,242,614 | 3/1966 | Thompson | 47/66 X |
| 3,654,903 | 4/1972 | Montgomery | 119/15 |
| 3,961,603 | 6/1976 | Gaddie | 119/15 |

Primary Examiner—Robert E. Bagwill
Attorney, Agent, or Firm—Harry E. Aine; Harvey G. Lowhurst

[57] ABSTRACT

In a composite horticultural system, a lower worm culture container contains a worm culture medium for growing worms and converting manure to worm casting type top soil. The top soil is used in a plant growing container mounted above the worm culture container. The environment over the plant growing medium is controlled by an environmental control means comprising a frame with replaceable panels. One set of panels comprises a sheet of translucent material for permitting sun light to pass therethrough and for retaining the heat within the plant growing container, whereas a second set of replacement panels comprises a slat arrangement for shading the plants and for passage therethrough of air for controlling the temperature within the plant growing container. A seed sprouting tray is arranged to be fitted between the bottom of the plant growing container and the worm culture container for using the darkness and warmth between the two media for sprouting of seeds which may then be transferred to the plant growing container. The composite horticultural device is useful as a teaching aid for teaching horticulture and/or as a starter and growing box for horticulture purposes.

11 Claims, 4 Drawing Figures

U.S. Patent  Apr. 10, 1979  4,148,154
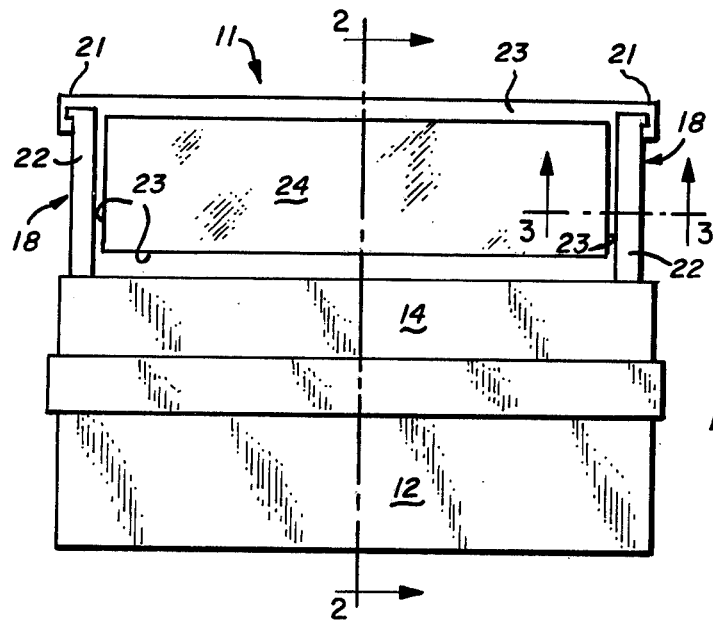
Fig_1
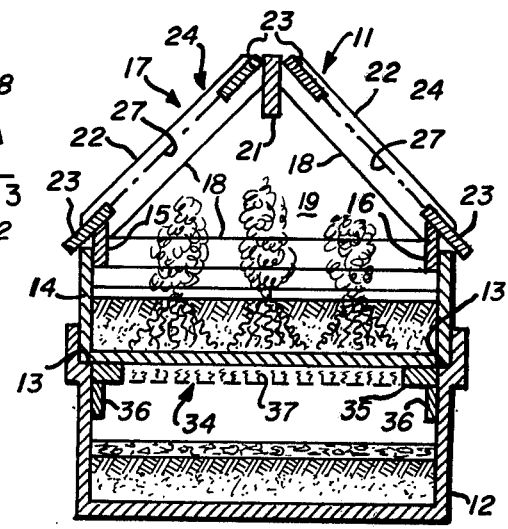
Fig_2
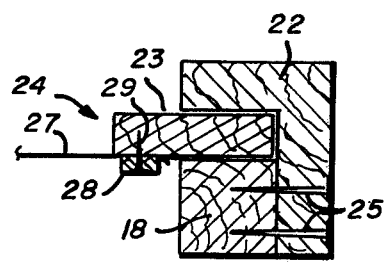
Fig_3
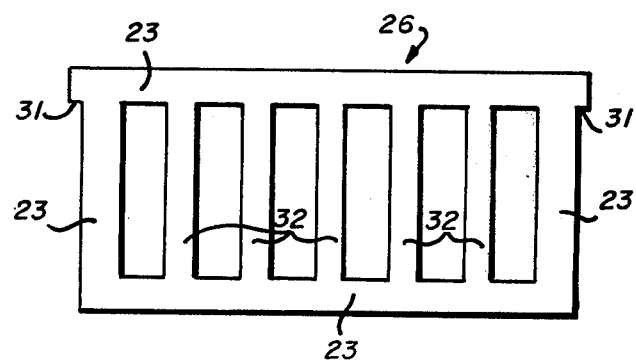
Fig_4

COMPOSITE HORTICULTURAL SYSTEM

BACKGROUND OF THE INVENTION

The present invention relates in general to horticulture and more particularly to a composite horticultural system useful as a training aid and/or for horticultural purposes.

DESCRIPTION OF THE PRIOR ART

Heretofore, separate containers have been employed for worm culture and for growth of plants. In addition, frameworks have been disposed over the plant growing medium for controlling the environment of the plant growing medium, such frameworks have included the use of translucent plastic sheets for passage of sun light therethrough onto the growing medium and the alternative of an array of slats for shading the growing medium and allowing air to pass therethrough.

However, there is a need both as a teaching aid and as a horticultural system for a composite system which can integrate the various components into an overall composite system such that all the individual components operate together in a most advantageous manner for approximating that of nature at its best.

SUMMARY OF THE PRESENT INVENTION

The principal object of the present invention is the provision of an improved horticultural system useful as a training aid and/or plant starting or growing system.

In one feature of the present invention, a plant growing container is disposed above a worm culture container and an environmental control structure is disposed over the plant growing medium for controlling the growing conditions therein. In this system, the worm culture, in the lower container, converts manure to a worm casting type top soil to be used as the growing medium in the second container and the plant growing environment in the second container is controlled by the environmental control means, whereby a particularly efficient composite horticultural system is obtained.

In another feature of the present invention, a seed sprouting tray is disposed between the bottom of the plant growing medium container and the worm culture medium within the worm culture container, whereby the darkness and warmth of the region between the two mediums is employed for sprouting of seeds.

In another feature of the present invention, the environmental control structure includes replaceable panels which may be either made of translucent air impermeable material or spaced opaque slats for controlling the amount of sun light incident on the plants in the growing container and for controlling the flow of air between the plant growing container and its surrounds.

Other features and advantages of the present invention will become apparent upon a perusal of the following specification taken in connection with the accompanying drawings wherein:

BRIEF DESCRIPTION OF THE DRAWINGS

FIG. 1 is a side elevational view of a composite horticultural system incorporating features of the present invention, FIG. 2 is a sectional view of a portion of the structure of FIG. 1 taken along line 2—2 in the direction of the arrows, FIG. 3 is an enlarged detailed cross-sectional view of a portion of the structure of FIG. 1 taken along line 3—3 in the direction of the arrows, and FIG. 4 is a plan view of a slat panel alternative portion of the system of FIGS. 1 and 2.

DESCRIPTION OF THE PREFERRED EMBODIMENTS

Referring now to FIGS. 1 and 2, there is shown the composite horticultural system 11 incorporating features of the present invention. The system 11 includes a worm culture container 12, open at the top and of generally rectangular shape. In a typical example, the depth is six inches, the width is twelve inches and the length is 25 inches. The upper lip of the container 12 is provided with an internal shoulder at 13 to receive and to support in nested relation the bottom of a growing medium container 14.

The growing medium container 14 is of generally rectangular shape, open at the upper end and provided at the upper lip with an internal shoulder 15 to receive and hold in nested relation the lower rectangular frame portion 16 of an environmental control framework 17.

The environmental control framework 17 includes a pair of upstanding triangular shaped end frame structures 18, a triangular opening of each frame structure is closed over at 19 by means of a translucent air impermeable sheet of plastic, as of 0.010 inch thick polyvinylchloride. The two triangular end frame members 18 are affixed together at their peaks by means of a longitudinal ridge pole 21 extending lengthwise of the frame structure 17. A generally L-shaped cross section retainer member 22 (see the detail of FIG. 3) is affixed over the upper side edges of the triangular frame members 18 so as to provide a gap between the frame member 18 and the overhanging portion of the L-shaped member 22 to slidably receive therewithin a rectangular frame portion 23 of a replaceable panel 24. The generally L-shaped cross section members 22 may be affixed to the frame 18 as by nails 25. The framework structure 17 includes a pair of such replaceable panels 24, one disposed on each side of the peak of the frame 17 and each sliding upwardly and downwardly at the inclined angle of frames 18 and retaining members 22 so that the panels may slide out for the complete exposure of the growing medium within the container 14 or for replacement by alternative lath panels 26 as shown in FIG. 4.

The translucent replaceable panels 24 include a sheet of air impermeable clear plastic or translucent plastic material 27 retainer at their outer lip portions to the inner lip of the rectangular frame 23, as by a plurality of battens 28 secured as by staples 29 to the frame 23. In a typical example, the translucent plastic material 27 of the panel 24 comprises a clear polyvinylchloride sheet of a thickness of 0.010 inch thick. Each of the panel frames 23 includes a tab portion 31 which abutts the upper ends of the L-shaped retainer members 22 so that the panels 24 do not slip through the retaining slots formed between frame members 18 and the overhanging retaining member 22. In the case of the lath panel 26, intermediate lath portions 32 extend between the opposite sides of the frame member 23 and are secured thereto as by adhesive.

A seed sprouting tray 34 is disposed between the bottom of the plant growing container 14 and the top of the soil formed in the worm culture container 12. The seed sprouting tray 34 comprises a rectangular frame member 35 carried from an internal shoulder or lip portion 36 extending at the inside at least along two sides of the worm culture container 12 near the upper lip. The seed sprouting frame 35 is open in the center and the open portion is covered by means of a mesh, such as a close stitched burlap sheet, cheese cloth, or nylon screen. The mesh 37 is secured to the frame 35 via staples at the outer periphery of the mesh 37. The bottoms of both the worm culture container 12 and the plant growing container 14 are perforated to permit water drainage therethrough while retaining the soil therewithin. In a typical example, the worm culture container 12 and the growing medium container 14 are made of, for example, redwood lath with four inch wide laths spaced by one-half inch spacing to permit water drainage therethrough.

In use, two inches of well aged horse manure is placed on the bottom of the worm culture container 12 and one pound of red hybrid earthworms is placed in the layer of manure and if desired the upper surface of the manure may be covered with brown leaves. In a few weeks, the layer of manure will be reduced in thickness and converted by the red worms to a layer approximately two inches thick of worm castings. These castings are then covered with another two inches of manure and perhaps soy bean flour as a worm food supplement, and in a few weeks the castings will increase in thickness by another two inches to a total thickness of approximately four inches. The castings may then be harvested and placed into the plant growing container 14 and therein mixed with approximately 25% by volume of sand to form the plant growing medium. The worm culture container can also be started again with another layer of manure so that the manure is continuously converted in the lower container to worm casting type top soil.

Seeds to be sprouted are placed on the seed sprouting tray 34 and the seeds are preferably covered with another layer of cheese cloth. When the seeds have sprouted to a sufficient degree in the dark and warm environment created between the worm culture medium and the growing medium, they may be transferred into the growing medium in the plant growing container 14.

The replaceable panels 24 are selected and employed in such a manner as to maintain optimum growing conditions within the growing container 14, considering the ambient environment. The containers 14 and 12 are watered as desired and the drainage from the plant growing container 14 into the worm culture container 12 serves to further dampen the seed sprouting tray 34.

The advantage of the composite horticultural system 11 of the present invention is that the growing conditions of the earth, with its various strata including the air, surface and subsurface, are duplicated on a small scale in the composite horticultural system 11 to provide ideal growing and seed germination conditions. Furthermore, the system is self-rejuvenating, as in nature, by the action of the worm culture unit 12. Elements in trace amounts may be added to the system 11 by making teas of various herbs and vegetation containing the desired trace elements and utilizing the teas for watering the growing medium, the sprouting seeds on the seed sprouting tray 34, and the worm culture medium wherein they are converted via the worms into the casting type top soil to be used as the growing medium in container 14. Thus, in one horticultural system 11, the earth's ecosystem relative to plant horticulture can be demonstrated to the student and/or employed for horticultural purposes.

What is claimed is:

1. In a composite horticultural system:
   first container means for containing a worm culture medium for growing worms and for converting manure to be placed therein to worm casting type top soil;
   second container means for containing a plant growing medium including worm casting type top soil produced in said first container means for growing of plants therein;
   environmental control means for affecting the temperature and growing conditions of plants planted within said top soil in said container means, said environmental control means being light transmissive for passage of sunlight therethrough to the plants;
   first mounting means for mounting said second container means over said first container means; and
   second mounting means for mounting said environmental control means over said second container means and to at least one of said first and second container means for support of said environmental control means from said container means to which said control means is mounted, whereby an integrated composite horticultural system is formed, which approximates the earth's ecosystem relative to horticulture.

2. The apparatus of claim 1 wherein said first container means is deeper than said second container means.

3. The apparatus of claim 1 wherein said first mounting means comprises an upper portion of said first container means shaped, dimensioned and arranged relative to the shape, dimensions and arrangement of said second container means for nesting a lower portion of said second container means within an upper portion of said first container means.

4. The apparatus of claim 1 wherein said second mounting means comprises an upper portion of said second container means shaped, dimensioned and arranged relative to the shape, dimensions and arrangement of said environmental control means for nesting a lower portion of said environmental control means within an upper portion of said second container means.

5. The apparatus of claim 1 wherein said environmental control means comprises a frame structure with replaceable panel means for controlling the flow of air and sun light through said panel means into said second container means.

6. The apparatus of claim 5 wherein one of said replaceable panel means comprises a frame member covered with a sheet of translucent material for flow of sun light therethrough while inhibiting the flow of air therethrough.

7. The apparatus of claim 5 wherein one of said replaceable panel means comprises a plurality of spaced opaque slats for partially restricting the flow of sun light therethrough while providing substantial air flow therethrough.

8. The apparatus of claim 1 including seed sprouter tray means for disposition between the bottom of said second container means and the worm culture medium to be disposed in said first container means for holding seeds for sprouting in the darkness and warmth existing between said first and second container means when mounted together in use.

9. The apparatus of claim 8 wherein said seed sprouter tray means comprises an open frame structure and a sheet of air and water permeable material covering said frame structure for supporting the seeds to be sprouted.

10. The apparatus of claim 9 including retaining lip means disposed within and affixed to said first container means for receiving and holding said seed sprouter tray means above the worm culture medium in said first container means.

11. In a method of demonstrating the earth's ecosystem relative to horticulture, the steps of:

placing manure and worms in a first container for growing the worms and for converting the manure to worm casting type top soil in said first container;

placing worm casting type top soil produced in said first container within a second container and planting plants in the worm casting type top soil in said second container for growth of the plants therein;

mounting a sunlight transmissive environmental control means over said second container and to one of said first and second containers for controlling the temperature and growing conditions of the plants planted within said second container; and mounting said second container over said first container to form an integrated composite horicultural system which approximates the earth's ecosystem relative to horticulture.

* * * * *